United States Patent [19]

Gajowski et al.

[11] Patent Number: 4,657,920
[45] Date of Patent: Apr. 14, 1987

[54] (1,2,4-TRIAZOL-1-YL)-2-THIAZOL-2-YL ETHANOL AS FUNGICIDES

[75] Inventors: Jan Gajowski, Oldenburg; Erik Regel, Wuppertal; Karl H. Büchel, Burscheid; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 715,144

[22] Filed: Mar. 22, 1985

[30] Foreign Application Priority Data

Apr. 7, 1984 [DE] Fed. Rep. of Germany ....... 3413173

[51] Int. Cl.$^4$ ................. A01N 43/653; C07D 249/08
[52] U.S. Cl. ..................... 514/365; 514/367; 514/368; 514/374; 514/375; 548/179; 548/205; 548/217; 548/235
[58] Field of Search ............... 548/205, 235, 179, 217; 514/365, 374, 367, 368, 375

[56] References Cited

U.S. PATENT DOCUMENTS 3,801,590 4/1974 Draber et al. .................. 548/205
4,548,945 10/1985 Holmwood et al. ............ 514/383

FOREIGN PATENT DOCUMENTS 2920374 11/1980 Fed. Rep. of Germany .

Primary Examiner—Donald G. Daus
Assistant Examiner—Stephen M. Kapner
Attorney, Agent, or Firm—Sprung Horn Kramer & Woods

[57] ABSTRACT 1,2,4-Triazol-1-yl-methyl-carbinols of the formula

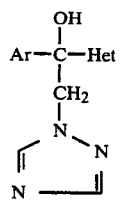

in which
  Ar is optionally substituted aryl, and
  Het is optionally substituted heteroaryl with at least 2 different hetero-atoms, or addition products thereof with plant-tolerated acids or metal salts, which possess fungicidal activity.

9 Claims, No Drawings

(1,2,4-TRIAZOL-1-YL)-2-THIAZOL-2-YL ETHANOL AS FUNGICIDES

The invention relates to new 1,2,4-triazol-1-yl-methyl-carbinols, a process for their preparation and their use as fungicides.

It has already been disclosed that certain heterocyclic nitrogen compounds, such as, for example, 6-methyl-2-oxo-dithiolo[4,5-b]-quinoxaline (compare DE-AS (German Published Specification) No. 1,100,372), or certain 1,2,4-triazol-1-ylmethyl-carbinols, such as, for example, 1-(4-biphenylyl)-1-(2-fluorophenyl)-2-(1,2,4-triazol-1-yl)-ethanol or 1-(4'-chloro-4-biphenylyl)-1-(4-chlorophenyl)-2-(1,2,4-triazol-1-yl)-ethanol (compare DE-OS (German Published Specification) No. 2,920,374 have fungicidal properties.

However, the action of these compounds is not always completely satisfactory in all fields of application, especially when low amounts are applied and the concentrations are low.

New 1,2,4-triazol-1-ylmethyl-carbinols of the general formula (I)

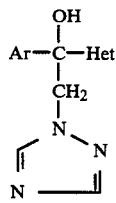

in which
Ar represents optionally substituted aryl and
Het represents optionally substituted heteroaryl with at least 2 different hetero-atoms,
and acid addition salts and metal salt complexes thereof which are tolerated by plants, have been found.

It has furthermore been found that the new 1,2,4-triazol-1-ylmethyl-carbinols of the general formula (I) and acid addition salts and metal salt complexes thereof which are tolerated by plants are obtained by a process in which oxiranes of the formula (II)

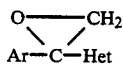

in which
Ar and Het have the abovementioned meaning, are reacted with alkali metal salts of 1,2,4-triazole, of the formula (III)

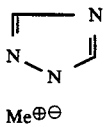

in which
Me⊕ represents an alkali metal cation, if appropriate in the presence of a diluent, and, if appropriate, an acid or a metal salt is then added on.

Finally, it has been found that the new 1,2,4-triazol-1-ylmethyl-carbinols of the general formula (I) and acid addition salts and metal salt complexes thereof which are tolerated by plants have fungicidal properties.

Surprisingly, the new 1,2,4-triazol-1-ylmethyl-carbinols of the general formula (I) have a better fungicidal activity than the compounds 6-methyl-2-oxo-1,3-dithiolo-[4,5-b]-quinoxaline, 1-(4-biphenylyl)-1-(2-fluorophenyl)-2-(1,2,4-triazol-1-yl)-ethanol or 1-(4'-chloro-4-biphenylyl)-1-(4-chlorophenyl)-2-(1,2,4-triazol-1-yl)-ethanol, which are known from the prior art and are closely related compounds chemically and/or from the point of view of their action.

Formula (I) provides a general definition of the new 1,2,4-triazol-1-ylmethyl-carbinols. Preferred compounds of the formula (I) are those
in which
Ar represents aryl which has 6 to 10 carbon atoms and is optionally monosubstituted or polysubstituted by identical or different substituents, possible substituents being: halogen, cyano, nitro, in each case straight-chain or branched alkyl, alkoxy or alkylthio with in each case up to 4 carbon atoms, and in each case straight-chain or branched halogenoalkyl, halogenoalkoxy or halogenoalkylthio with in each case up to 4 carbon atoms and up to 9 identical or different halogen atoms, and
Het represents a 5-membered or 6-membered heterocyclic radical which has at least 2 different hetero-atoms and is optionally monosubstituted or polysubstituted by identical or different substituents and/or benzo-fused, possible hetero-atoms being: nitrogen as well as oxygen and/or sulphur, and possible substituents being: halogen, straight-chain or branched alkyl with up to 4 carbon atoms, cycloalkyl with 3 to 7 carbon atoms, straight-chain or branched halogenoalkyl with up to 4 carbon atoms and up to 9 identical or different halogen atoms, and aryl which has 6 to 10 carbon atoms and is optionally monosubstituted or polysubstituted by identical or different substituents, possible substituents on the aryl being the substituents mentioned in the case of Ar.

Particularly preferred compounds of the formula (I) are those
in which
Ar represents phenyl or naphthyl which is optionally mono-, di- or tri-substituted by identical or different substituents, possible substituents being: fluorine, chlorine, bromine, cyano, nitro, methyl, ethyl, propyl, butyl, methoxy, ethoxy, methylthio, trifluoromethyl, trifluoromethoxy, trifluoromethylthio and
Het represents a heterocyclic radical of the formula

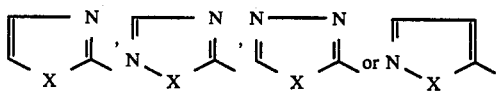

which can optionally also be benzo-fused and which is optionally mono-, di or tri-substituted by identical or different substituents from the group comprising methyl, ethyl, cyclopropyl, cyclohexyl, fluorine, chlorine, bromine, trifluoromethyl, chlorodifluoromethyl, dichlorofluoromethyl, trichloromethyl, dichloromethyl, chloromethyl and optionally mono-, di or tri-substituted phenyl,
X in each case representing oxygen or sulphur and possible substituents on the phenyl being those mentioned in the case of Ar.

The following 1,2,4-triazol-1-ylmethyl-carbinols of the general formula (I) may be mentioned specifically, in addition to the compounds mentioned in the preparation examples:
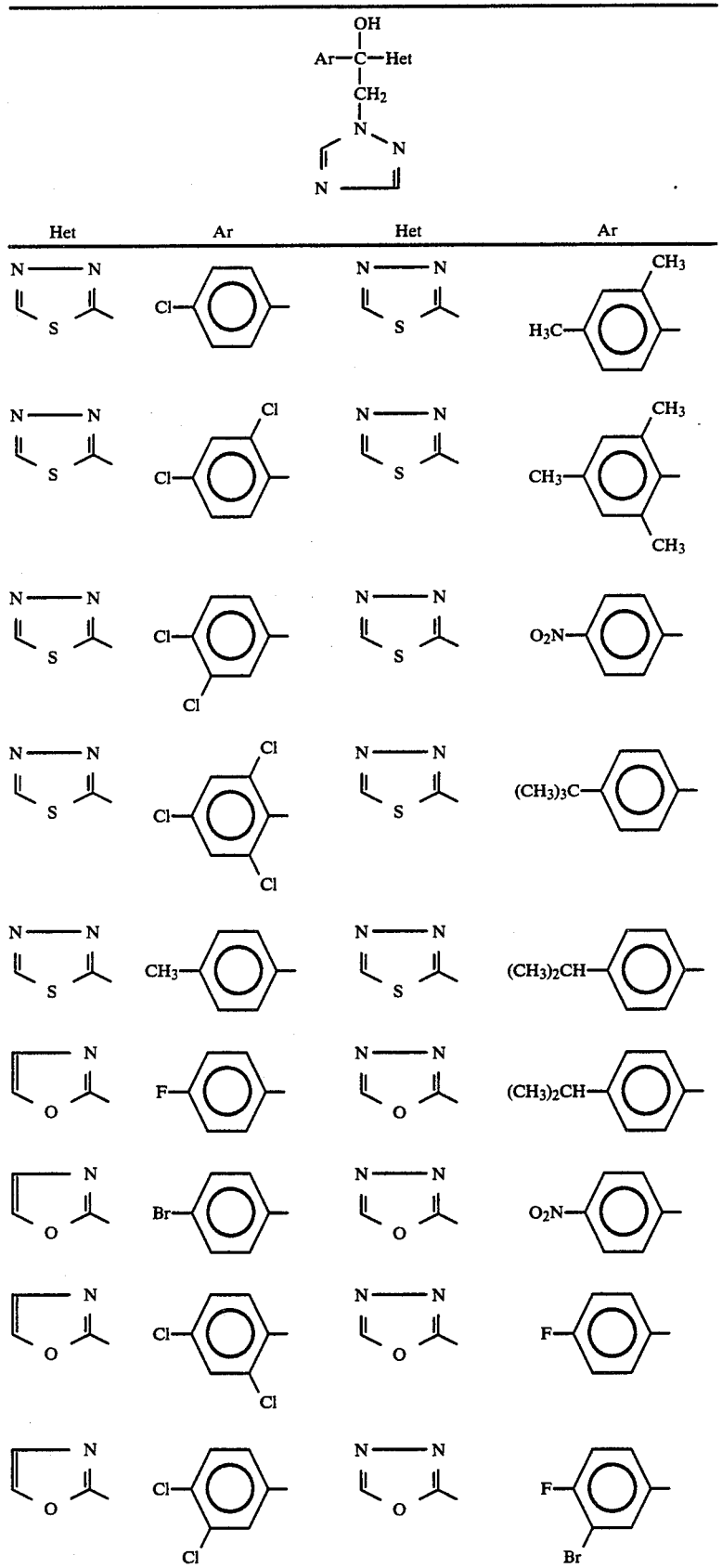

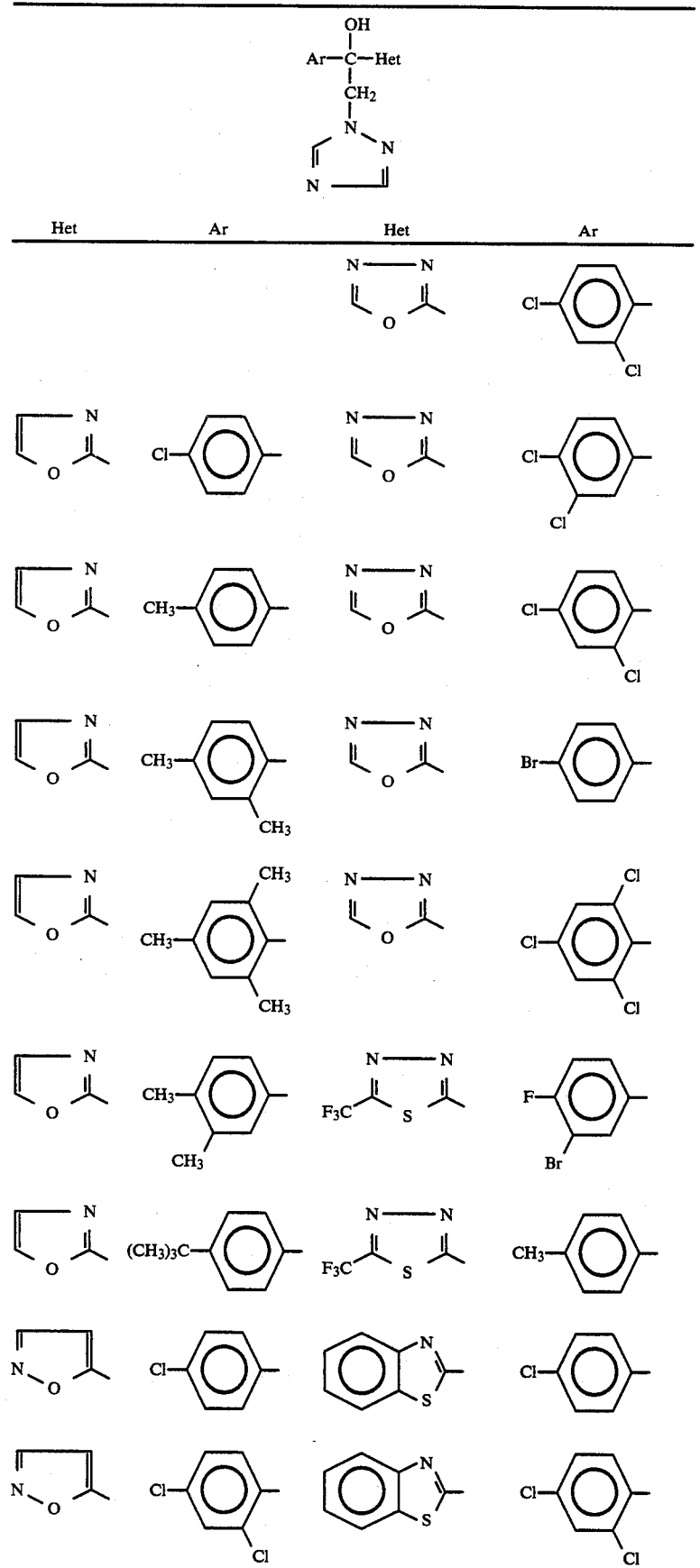

-continued
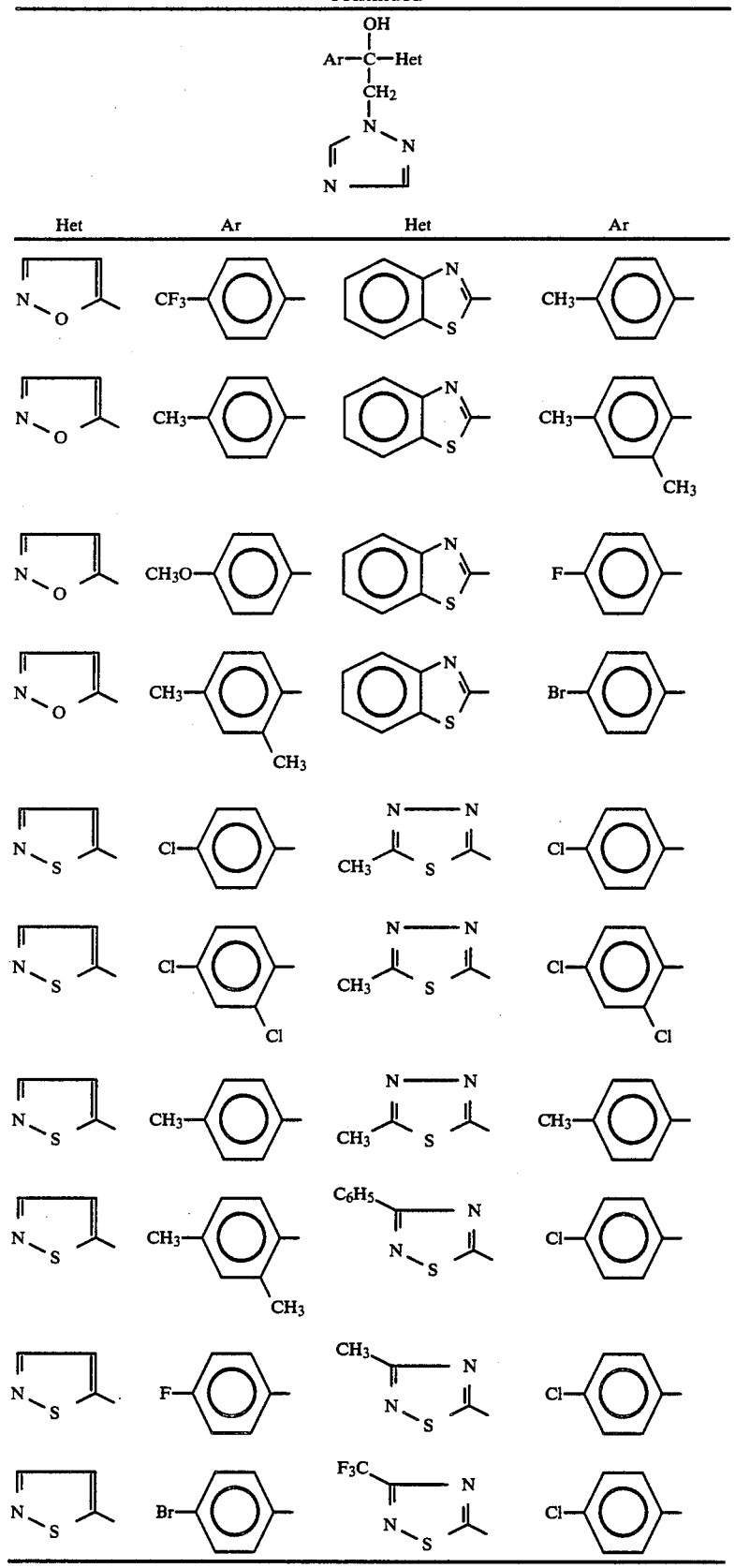
If, for example, 2-(4-chlorophenyl)-2-thiazol-2-yloxirane and the sodium salt of 1,2,4-triazole are used as starting substances, the course of the reaction in the

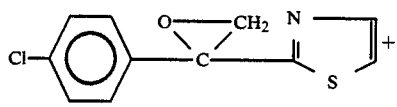

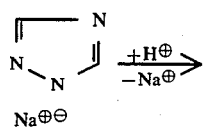

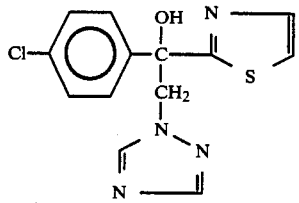

Formula (II) provides a general definition of the oxiranes required as starting substances for carrying out the process according to the invention. In this formula (II) Ar and Het preferably represent those radicals which have already been mentioned as preferred for these substituents in the description of the substances of the formula (I) according to the invention.

The oxiranes of the formula (II) are not yet known. They are obtained, however, by processes which are known in principle. See U.S. Pat. No. 4,548,945 in which heterocyclic compounds of the formula (IV)

Het—X  (IV)

in which

Het has the abovementioned meaning and

X represents hydrogen or halogen, in particular chlorine or bromine, are first reacted with aldehydes of the formula (V)

Ar—C—H  (V)

in which

Ar has the abovementioned meaning, in a first stage in the presence of a strong base, such as, for example, n-butyl-lithium, and in the presence of a diluent, such as, for example, ether or tetrahydrofuran, between −100° C. and −70° C., and the carbinols thus obtainable, of the formula (VI)

Ar—CH—Het  (VI)

in which

Ar and Het have the abovementioned meaning, are oxidized with an oxidizing agent, such as, for example, sodium dichromate, in a second stage in the presence of a catalyst, such as, for example, acetic acid, in the generally customary manner, and the ketones thus obtainable, of the formula (VII)

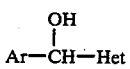

Ar—C—Het  (VII)

in which

Ar and Het have the abovementioned meaning, are epoxidized with trimethylsulphonium iodide of the formula (VIII)

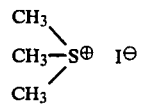

in a third stage, likewise in the presence of a strong base, such as, for example, potassium tert.-butylate, and in the presence of a diluent, such as, for example, dimethylsulphoxide, at temperatures between −20° C. and +50° C.

Formula (III) provides a general definition of the alkali metal salts of 1,2,4-triazole also required as starting substances for carrying out the process according to the invention. In this formula (III), Me$^\oplus$ preferably represents a sodium or potassium cation.

The alkali metal salts of the triazole, of the formula (III), the halogenoheterocyclic compounds of the formula (IV), the aromatic aldehydes of the formula (V) and the trimethylsulphonium iodide of the formula (VIII) are generally known compounds of organic chemistry.

Possible diluents for carrying out the process according to the invention are, in principle, inert organic solvents. These include, preferably, alcohols, such as, for example, ethanol, propanol or methoxyethanol, ketones, such as acetone or butanone, nitriles, such as acetonitrile or propionitrile, aromatic hydrocarbons, such as benzene or toluene, and amides, such as, for example, dimethylformamide.

The reaction temperatures can be varied within a substantial range in carrying out the process according to the invention. In general, the reaction is carried out between 0° C. and +200° C., preferably between +60° C. and +150° C.

In carrying out the process according to the invention, 1 to 3 moles, preferably 1 to 2 moles, of alkali metal salt of 1,2,4-triazole, of the formula (III), are in general employed per mole of oxirane of the formula (II). The alkali metal salt of 1,2,4-triazole, of the formula (III), can also be produced in situ, by first reacting 1,2,4-triazole and a corresponding amount of a strong alkali metal base, such as, for example, a sodium or potassium alcoholate or sodium hydride or potassium hydride with one another and adding the oxirane of the formula (II) to this reaction batch. The end products are worked up and isolated by generally customary methods.

The following acids can preferably be used for the preparation of acid addition salts of the compounds of the formula (I) which are tolerated by plants: the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV and VIII are preferably used for the preparation of metal salt complexes of the compounds of the formula (I), examples of metals which may be mentioned being copper, zinc, manganese, magnesium, tin, iron and nickel. Possible anions of the salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compounds of the formula (I). The metal salt complexes can be isolated in a known manner, for example by filtration, and if appropriate purified by recrystalization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating cereal diseases, such as, for example, against the powdery mildew of barley causative organism (*Erysiphe graminis*) or against the brown rust of wheat causative organism (*Puccinia recondita*), and also for combating plant diseases in vegetable growing, such as, for example, against the powdery mildew of cucumber causative organism (*Sphaerotheca fuliginea*). The active compounds according to the invention also exhibit an outstanding action against pathogens of rice diseases, such as, for example, against the rice spot disease causative organism (*Pyricularia oryzae*), and in addition, when applied in appropriate amounts, also exhibit a good insecticidal and plant growth-regulating action.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs and azo- or metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentration in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

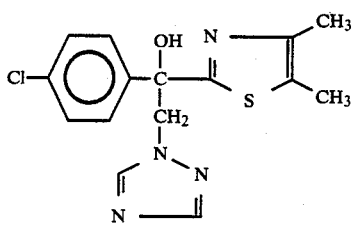

2.1 g (0.03 mole) of 1,2,4-triazole are added in portions to a well-stirred suspension of 0.9 g (0.03 mole) of 80% pure sodium hydride in 40 ml of dimethylformamide. (A further portion is added only after the evolution of hydrogen in each case has subsided).

When the addition has ended, the mixture is stirred at room temperature for 30 minutes. A solution of 8.0 g (0.03 mole) of 2-(4-chlorophenyl)-2-(4,5-dimethylthiazol-2-yl)-oxirane in 10 ml of dimethylformamide is then added dropwise at room temperature and the mixture is subsequently heated at 80° C. for 3 hours.

For working up, the cooled reaction mixture is poured onto about 200 g of ice and extracted several times with 50 ml of methylene chloride each time. The combined organic phases are washed with water, dried over sodium sulphate and concentrated in vacuo. The residue is recrystallized from hexane/carbon tetrachloride. 8.4 g (83% of theory) of 1-(4-chlorophenyl)-1-(4,5-dimethylthiazol-2-yl)-2-(1,2,4-triazol-1-yl)-ethanol of melting point 174° C. are obtained.

Preparation of the starting compound

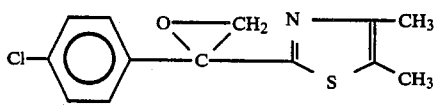

10.1 g (0.04 mole) of (4-chlorophenyl)-(4,5-dimethylthiazol-2-yl)-methanone and 8.6 g (0.042 mole) of trimethylsulphonium iodide are dissolved in 100 ml of anhydrous dimethylsulphoxide. A solution of 4.7 g (0.042 mole) of potassium tert.-butanolate in 30 ml of dimethylsulphoxide is added dropwise in the course of 5 minutes and the mixture is subsequently stirred for 20 minutes, during which the internal temperature should not exceed 25° C.

The mixture is diluted with 300 ml of ice-water and extracted three times with 50 ml of ether, and the organic phase is washed with 100 ml of water and dried over sodium sulphate. After the solvent has been stripped off in vacuo, 9.7 g (90% of theory) of 2-(4-chlorophenyl)-2-(4,5-dimethylthiazol-2-yl)-oxirane are obtained as an oil.

$^1$H-NMR (60 MHz, CDCl$_3$, ppm): $\delta$=2.36 (6H,s, CH$_3$ on C-4 and C-5), 3.16, 1.62 (2H, d, J=6 Hz; CH$_2$) and 7.42 (4H, d, 4-chlorophenyl-H)

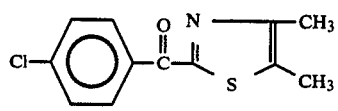

7.5 g (0.025 mole) of sodium dichromate dihydrate are dissolved in 50 ml of glacial acetic acid, with warming, the solution is cooled to 20° C. and mixed with a solution of 12.7 g (0.05 mole) of (4-chlorophenyl)-(4,5-dimethylthiazol-2-yl)-methanol in 30 ml of glacial acetic acid, and the mixture is then heated under reflux for 1 hour.

After cooling to room temperature, the mixture is poured onto 500 g of ice and extracted three times with 50 ml of methylene chloride each time, and the combined organic extracts are washed with saturated sodium bicarbonate solution and water. After drying over sodium sulphate, the solvent is distilled off under reduced pressure and its residue is recrystallized from ether. 11.3 g (90% of theory) of (4-chlorophenyl)-(4,5-dimethylthiazol-2-yl)-methanone of melting point 97° C. are obtained.

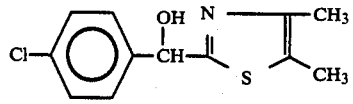

68 ml of a 1.55 molar n-butyl-lithium solution in n-hexane (0.105 mole) are added dropwise to a solution of 11.5 g (0.1 mole) of 4,5-dimethylthiazole in 100 ml of anhydrous ether at −70° C. in the course of 30 minutes, under a nitrogen atmosphere and with stirring. The mixture is subsequently stirred at this temperature for 30 minutes, and a solution of 14.0 g (0.1 mole) of 4-chlorobenzaldehyde in 50 ml of ether is then added in the course of 20 minutes. During this addition, the temperature is kept below −50° C., by cooling; the suspension is subequently stirred at room temperature for a further 30 minutes.

Thereafter, about 50 ml of saturated ammonium chloride solution are added dropwise, the aqueous phase is extracted twice with 50 ml of ether each time and the combined organic phases are dried over sodium sulphate and concentrated in vacuo. After 12 hours, the oil which remains solidifies. 21.3 g (84% of theory) of (4-chlorophenyl)-(4,5-dimethylthiazol-2-yl)-methanol of melting point 107° C. are obtained by recrystallization from petroleum ether (60°–75° C.).

The following (1,2,4-triazol-2-yl)-methylcarbinols of the general formula (I) are obtained in a corresponding manner and in accordance with the general preparation instructions:

15

$$\begin{array}{c} \text{OH} \\ | \\ \text{Ar}-\text{C}-\text{Het} \\ | \\ \text{CH}_2 \\ | \\ \text{N} \\ \end{array} \quad \text{(I)}$$

(with triazole ring attached to N)

| Example No. | Ar | Het | Physical properties |
|---|---|---|---|
| 2 | 4-Cl-phenyl | N=C(−)−S−CH=CH (thiazoline) | Melting point: 125° C. |
| 3 | 3,4-di-Cl-phenyl | N=C(CH₃)−S−C(CH₃)= | Melting point: 200° C. |
| 4 | 3,4-di-Cl-phenyl | N=C(CH₃)−S−C(CH₃)= | Melting point: 192° C. |
| 5 | 4-Cl-phenyl | N=C(−)−S−C(Cl)=C(Cl) | Melting point: 210° C. |
| 6 | 4-F, 3-Br-phenyl | N=C(CH₃)−S−C(CH₃)= | Melting point: 171° C. |
| 7 | phenyl | N=C(−)−S−CH=CH | Oil |
| 8 | 4-F-phenyl | N=C(CH₃)−S−C(CH₃)= | Melting point: 146° C. |
| 9 | 4-CH₃-phenyl | N=C(−)−S−CH=CH | Melting point: 157° C. |
| 10 | 4-CH₃-phenyl | N=C(CH₃)−S−C(CH₃)= | Melting point: 168° C. |
| 11 | 4-F-phenyl | N=C(−)−S−CH=CH | Melting point: 127° C. |

16

USE EXAMPLES

The compounds shown below are employed as comparison substances in the following use examples:

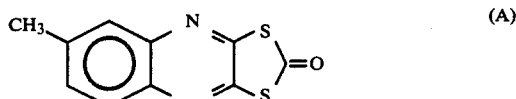

6-Methyl-2-oxo-1,3-dithiolo-[4,5-b]-quinoxaline (known from DAS (German Published Specification) No. 1,100,372)

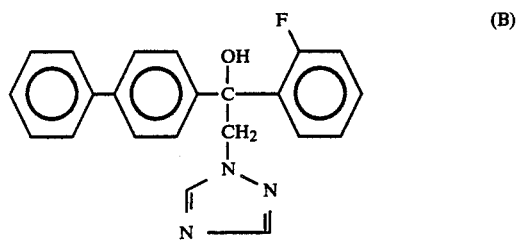

1-(4-Biphenylyl)-1-(2-fluorophenyl)-2-(1,2,4-triazol-1-yl)-ethanol

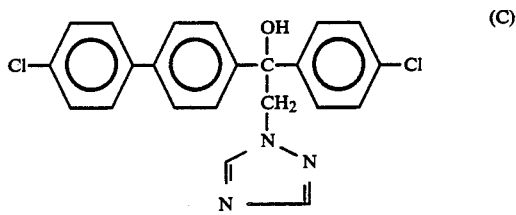

1-(4'-Chloro-4-biphenylyl)-1-(4-chlorophenyl)-2-(1,2,4-triazol-1-yl)-ethanol
(known from DE-OS (German Published Specification) No. 2,920,374).

Example A

Sphaerotheca test (cucumber)/protective
Solvent: 4.7 parts of weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 1, 2 and 5.

Example B

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to the following preparation example: 1.

Example C

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 2 and 3.

It is understood that the specification and examples are illustrative but not limitative of the present invention and that other embodiments within the spirit and scope of the invention will suggest themselves to those skilled in the art.

We claim:

1. A 1,2,4-triazol-1-yl-methyl-carbinol of the formula

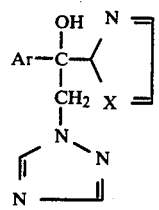

in which
Ar is phenyl or naphthyl which is optionally mono-, di- or tri-substituted by fluorine, chlorine, bromine, cyano, nitro, methyl, ethyl, propyl, butyl, methoxy, ethoxy, methylthio, trifluoromethyl, trifluoromethoxy and/or trifluoromethylthio.

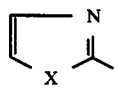

can optionally be benzo-fused and optionally mono-, di-, or tri-substituted by methyl, ethyl, cyclopropyl, cyclohexyl, fluorine, chlorine, bromine, trifluoromethyl, chlorodifluoromethyl, dichlorofluoromethyl, trichloromethyl, dichloromethyl, chloromethyl and/or phenyl optionally mon-, di- or tri-substituted by those substituents mentioned in the case of Ar, and
X is oxygen or sulphur,
or an addition product thereof with a plant-tolerated acid or metal salt.

2. A compound according to claim 1, wherein such compound is 1-(4-chlorophenyl)-1-(4,5-dimethyl-thiazol-2-yl)-2-(1,2,4-triazol-1-yl)-ethanol of the formula

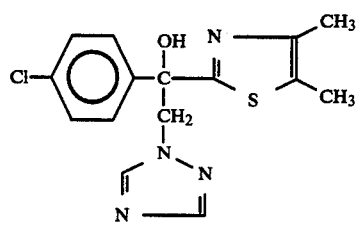

or an addition product thereof with a plant-tolerated acid or metal salt.

3. A compound according to claim 1, wherein such compound is 1-(4-chlorophenyl)-1-(thiazol-2-yl)-2-(1,2,4-triazol-1-yl)-ethanol of the formula

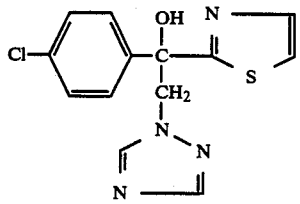

or an addition product thereof with a plant-tolerated acid or metal salt.

4. A compound according to claim 1, wherein such compound is 1-(2,4-dichlorophenyl)-1-(4,5-dimethylthiazol-2-yl)-2-(1,2,4-triazol-1-yl)-ethanol of the formula

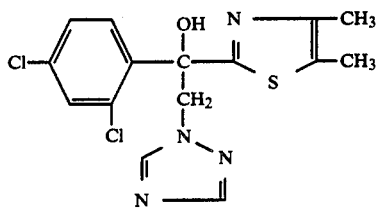

or an addition product thereof with a plant-tolerated acid or metal salt.

5. A compound according to claim 1, wherein such compound is 1-(4-chlorophenyl)-1-(4,5-dichloro-thiazol-2-yl)-2-(1,2,4-triazol-1-yl)-ethanol of the formula

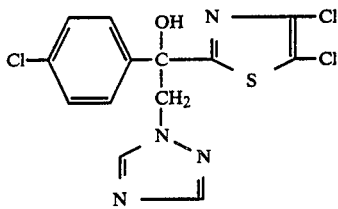

or an addition product thereof with a plant-tolerated acid or metal salt.

6. A fungicidal composition comprising a fungicidally effective amount of a compound or addition product according to claim 1 and a diluent.

7. A method of combating fungi which comprises applying to such fungi or to a fungus habitat a fungicidally effective amount of a compound or addition product according to claim 1.

8. The method according to claim 7, wherein such compound is
1-(4-chlorophenyl)-1-(4,5-dimethyl-thiazol-2-yl)-2-(1,2,4-triazol-1-yl)-ethanol,
1-(4-chlorophenyl)-1-(thiazol-2-yl)-2-(1,2,4-triazol-1-yl)-ethanol,
1-(2,4-dichlorophenyl)-1-(4,5-dimethyl-thiazol-2-yl)-2-(1,2,4-triazol-1-yl)-ethanol or
1-(4-chlorophenyl)-1-(4,5-dichloro-thiazol-2-yl)-2-(1,2,4-triazol-1-yl)-ethanol,
or an addition product thereof with a plant-tolerated acid or metal salt.

9. An oxirane of the formula

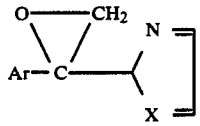

in which
Ar is phenyl or naphthyl which is optionally mono-, di- or tri-substituted by fluorine, chlorine, bromine cyano, nitro, methyl, ethyl, propyl, butyl, methoxy, ethoxy, methylthio, trifluoromethyl, trifluoromethoxy and/or trifluoromethylthio, and

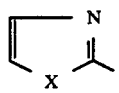

can optionally be benzo-fused and optionally mono-, di-, or tri-substituted by methyl, ethyl, cyclopropyl, cyclohexyl, fluorine, chlorine, bromine, trifluoromethyl, chlorodifluoromethyl, dichlorofluoromethyl, trichloromethyl, dichloromethyl, chloromethyl and/or phenyl optionally mon-, di- or tri- those substituents mentioned in the case of Ar.

* * * * *

UNITED STATES PATENT AND TRADEMARK OFFICE
CERTIFICATE OF CORRECTION

PATENT NO. : 4,657,920

DATED : April 14, 1987

INVENTOR(S) : Jan Gajowski, et al.

It is certified that error appears in the above-identified patent and that said Letters Patent is hereby corrected as shown below:

| | |
|---|---|
| Col. 7, last line | After "the" insert --process according to the invention can be represented by the following equation:-- |
| Col. 11, line 24 | Correct spelling of --recrystallization-- |
| Col. 13, line 4 | Delete "concentration" and substitute --concentrations-- |
| Col. 14, line 5 | Delete "1.62" and substitute --3.62-- |

Signed and Sealed this

Eighteenth Day of August, 1987

Attest:

DONALD J. QUIGG

Attesting Officer

Commissioner of Patents and Trademarks